United States Patent [19]

DeVore et al.

[11] Patent Number: 4,888,017
[45] Date of Patent: Dec. 19, 1989

[54] APPARATUS OF CONTROLLING EUSTACHIAN TUBE FUNCTION

[75] Inventors: Richard A. DeVore, Richfield; Sam E. Kinney, Moreland Hills, both of Ohio

[73] Assignee: The Cleveland Clinic Foundation, Cleveland, Ohio

[21] Appl. No.: 73,504

[22] Filed: Jul. 15, 1987

[51] Int. Cl.⁴ .............................................. A61F 2/18
[52] U.S. Cl. ..................................................... 623/10
[58] Field of Search ................... 623/10, 11, 12, 14, 623/66; 128/1 R, DIG. 25, 79, 784, 334 R, 335.5, 746, 303.11, 305; 604/8

[56] References Cited

U.S. PATENT DOCUMENTS 4,407,278  10/1983  Burton et al. .................... 128/79 A
4,608,051  8/1986  Reck et al. .......................... 623/10

OTHER PUBLICATIONS

Wright; Preliminary Results with use of an Eustachian Tube Prothesis; Jan. 25, 1976, pp. 207–214.

Primary Examiner—Richard J. Apley
Assistant Examiner—David J. Isabella
Attorney, Agent, or Firm—Fay, Sharpe, Beall, Fagan, Minnich & McKee

[57] ABSTRACT

A proshesis apparatus method for implanting the apparatus, and method for controlling eustachian tube function includes an inflatable member dimensioned for at least partial receipt in a patient's eustachian tube. The inflatable member is operatively connected to means for selectively and volitionally inflating and deflating the member to close and open the eustachian tube. The inflating and deflating means preferably has a manually actuated pump disposed in subcutaneous tissue behind the ear and on the skull that communicates with the inflatable member. A reservoir means is placed in a surgically created mastoid cavity used for implanting the prosthesis. Alternatively, the reservoir means is formed as a portion of the pump. The eustachian tube function is controlled through selective inflation and deflation of the inflatable member to close and open the eustachian tube in a manner that simulates a normal, healthy eustachian tube. Further, the prosthesis apparatus allows volitional aeration of the middle ear space via control of eustachian tube opening and closing by a valve-like mechanism.

11 Claims, 1 Drawing Sheet

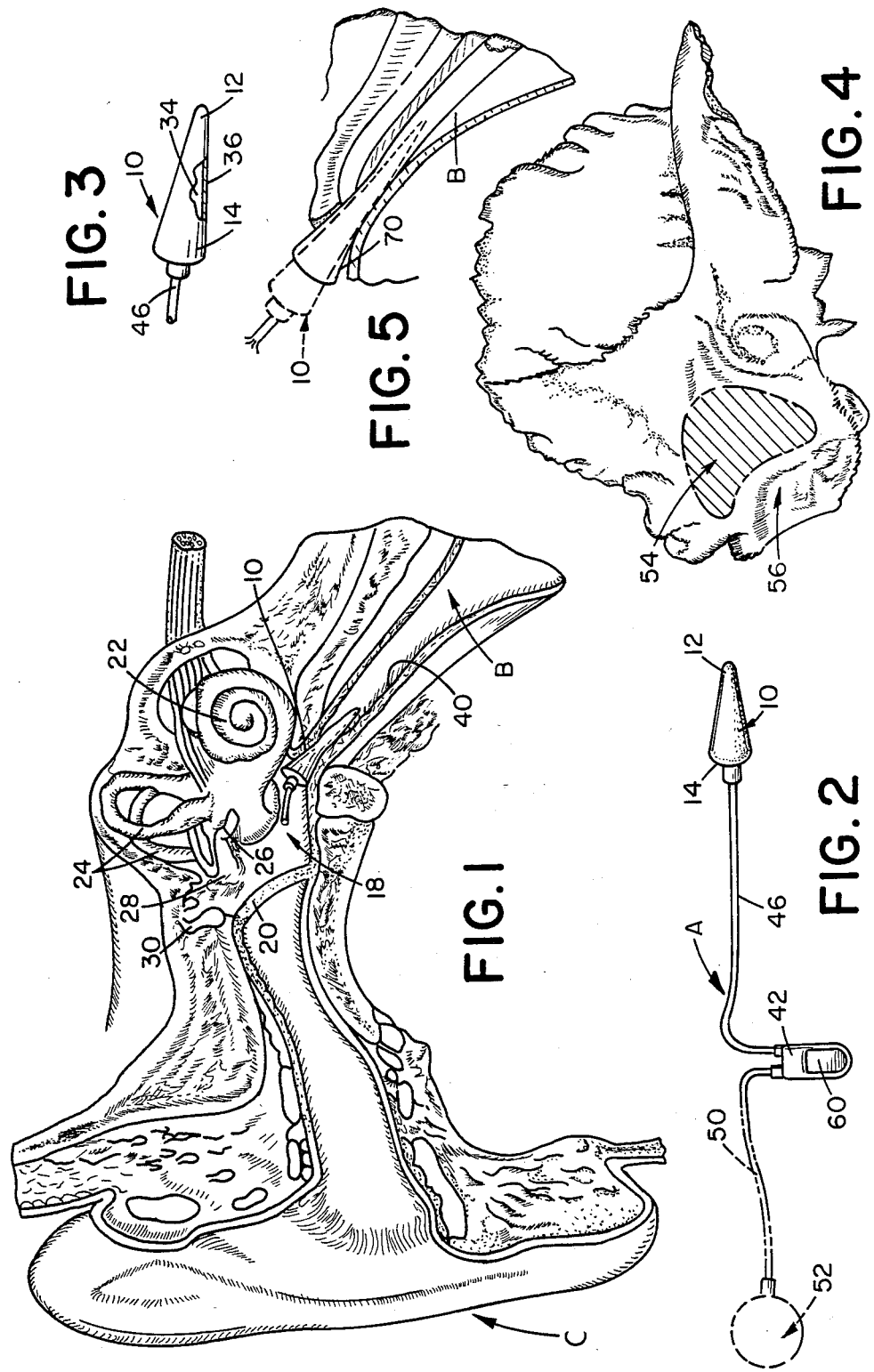

APPARATUS OF CONTROLLING EUSTACHIAN TUBE FUNCTION

BACKGROUND OF THE INVENTION

This invention pertains to the art of medical prostheses and more particularly to a prosthesis and method for controlling eustachian tube function, including but not limited to treating an abnormally patulous eustachian tube.

The invention is particularly applicable to a prosthesis disposed in one end of the eustachian tube adjacent the middle ear and will be described with particular reference thereto. However, it will be appreciated that the invention has broader applications and may be advantageously employed in other areas of the eustachian tube.

There is a spectrum of eustachian tube disorders ranging from abnormal chronic closure to abnormal constant patency. Persons suffering from a dysfunctional or chronically closed eustachian tube are exposed to problems related to chronic negative pressure in the middle ear space. Although not exclusive, a list of problems associated with a dysfunctional or chronically closed eustachian tube includes serous otitis media, chronic otitis media, tympanic membrane retraction, cholesteatoma formation and hearing loss. Oftentimes, a dysfunctional or chronically closed eustachian tube is encountered during middle ear surgery.

The Wright, III - U.S. Pat. No. 4,015,607 issued Apr. 5, 1977 describes in greater detail some of the problems and various methods devised for restoring aeration to the middle ear cavity. For purposes of brevity, that patent is hereby incorporated by reference to illustrate other procedures and apparatus used to maintain patency of the eustachian tube.

At the other end of the spectrum of eustachian tube disorders, a person suffering from an abnormally open, or patulous, eustachian tube is exposed to varied annoyances and problems resulting from free communication between the middle ear and the nasopharynx. The patulous eustachian tube is often associated with weight loss, neuromuscular disorders, and other chronic illnesses. The loss of soft tissue surrounding the eustachian tube is thought to be the primary reason for the patulous eustachian tube, although all the causes and reasons for the resulting condition may not be completely understood.

Symptoms associated with the condition include autophony, very simply described as the situation in which a patient hears his own breath and voice. Patients afflicted with a patulous eustachian tube also describe a feeling of fullness or blockage in the ear. In a normal, healthy patient the middle ear is usually maintained at a slightly negative pressure. Those afflicted with the condition under discussion, though, have their middle ear exposed to atmospheric pressure due to the open passageway and free communication with the nasopharynx. Thus, the feeling of fullness or blockage is believed to result from this pressure situation, namely, absence of a slightly negative pressure. Still other symptoms associated with a patulous eustachian tube can be detailed but those noted above are the most common problems associated with this condition.

A number of patients with these patulous eustachian tube symptoms have been diagnosed as neurotic or psychotic as reported by Pulec and Hahn, Jr. in *Otolaryngological Clinics of North America*, February 1970.

Thus, the concern and problems linked with a patulous eustachian tube dictate the need for a reliable solution. The November, 1982 Vol. 108 issue of *Archives of Otolaryngology* describes in an article by Virtanan and Palva a variety of suggested remedies for a patient suffering from a patulous eustachian tube. Among these include a prescription for weight increase to replace the tissue mass depleted by the weight loss. Another treatment prescribed is insufflation of boric acid and salicylic acid powder into the pharyngeal orifice of the eustachian tube. Yet another treatment involves infusion of an absorbable gelatin sponge solution into the eustachian tube. Still another proposed solution that has met with some limited success is the injection of Teflon material (a registered trademark of E. I. DuPont de Nemours and Company) at the anterior-inferior margin of the eustachian tube orifice. This treatment has been discontinued due to fatal injections of the internal carotid artery. Each of these other treatments has its minor successes but also suffers from various drawbacks.

Those afflicted with a patulous eustachian tube, as well as those treating the condition, consider the above-noted remedies to still fall far short of an adequate solution. Likewise, those persons afflicted with a dysfunctional or chronically closed eustachian tube and those treating the condition find present solutions incomplete. The subject invention is deemed to provide a prosthesis and method that will adequately treat the conditions and overcome the drawbacks associated with the noted remedies.

SUMMARY OF THE INVENTION

The present invention contemplates an apparatus for controlling eustachian tube function, an improved apparatus for treating a patulous eustachian tube, method of treating the conditions, and method of implanting the apparatus.

According to the subject invention, there is provided a prosthesis including an inflatable member having a dimension adapted to selectively control eustachian tube function. A means for selectively inflating and deflating the inflatable member alternately prevents and permits communication through the eustachian tube.

According to a more limited aspect of the invention, the inflatable member has a generally tapered conformation over its longitudinal dimension so that a first end is received in the eustachian tube and a second enlarged end is received in the middle ear.

According to a further aspect of the invention, the inflating and deflating means includes a pump means disposed on an exterior surface of the skull beneath the skin.

According to another aspect of the invention, the inflating and deflating means includes a reservoir means. A preferred embodiment forms the reservoir means as an integral portion of the pump means. Another preferred embodiment receives the reservoir means in a hollowed area of the mastoid.

According to an alternate aspect of the invention, a method of implanting the prosthesis includes placing the inflatable member at least partially in the eustachian tube. Additionally, the pump means is placed on an exterior surface of the skull.

According to an alternate aspect of the invention, a method for controlling eustachian tube function with a selectively inflatable prosthesis includes inflating the prosthesis member to block communication through the eustachian tube and deflating the prosthesis member to open communication through the eustachian tube.

Still further, the method of treating the conditions includes maintaining the prosthesis member in an inflated condition for a greater period of time than in a deflated condition.

A principal advantage of the invention is a reliable prosthesis that closely simulates the action of a healthy eustachian tube.

Another advange of the invention is volitional control of middle ear ventilation by the patient.

Yet another advantage of the invention is the simplified apparatus for treating these conditions.

Yet another advantage of the invention resides in the method of implanting a eustachian tube prosthesis.

A still further advantage of the invention is realized in the method for treating a patient who has either a chronically closed or abnormally patulous eustachian tube.

Still other advantages and benefits will become apparent to those skilled in the art upon a reading and understanding of the following detailed description.

BRIEF DESCRIPTION OF THE DRAWINGS

The invention may take physical form in certain parts and arrangements of parts, preferred embodiments of which will be described in detail in this specification and illustrated in the accompanying drawings which form a part hereof, and wherein:

FIG. 1 is a vertical sectional view of an ear illustrating proposed placement of the inflatable member of the subject prosthesis in the eustachian tube adjacent the middle ear;

FIG. 2 generally illustrates the prosthesis device with an alternate construction of the reservoir shown in phantom;

FIG. 3 is an enlarged view of the inflatable member of the prosthesis;

FIG. 4 is a side elevational view of a right temporal bone in which a mastoid cavity is formed through exenteration of the cells in the shaded region for implantation of the prosthesis and receipt of the reservoir means; and, FIG. 5 is an enlarged perspective view illustrating a modified stent used in conjunction with the inflatable member.

DETAILED DESCRIPTION OF THE PREFERRED EMBODIMENTS AND METHODS

Referring now to the drawings wherein the showings are for purposes of illustrating the preferred embodiments and methods of the invention only and not for purposes of limiting same, the FIGURES show a prosthesis A adapted for implantation in the eustachian tube B of a patient's ear C.

More specifically, the prosthesis A as shown in FIG. 2 includes an elongated member 10 dimensioned for partial receipt in the eustachian tube B. A first end 12 of the member has a reduced lateral dimension compared to that of the second end 14. Preferably, and for ease of construction, the member has a generally tapered conformation over its length extending from its enlarged dimension at the second end to the narrowed first end. Of course, still other conformations can be used within the spirit and scope of the subject invention. For example, the member may be formed as a pair of different diameter cylindrical portions as an alternative to the generally tapered or carrot-shaped member.

The generally carrot-shaped member permits receipt of the first end in the eustachian tube. The second end 14, on the other hand, is too large for the eustachian tube and extends into the middle ear cavity 18. The enlarged second end 14 is designed to retain the member at the interface between the eustachian tube and the middle ear cavity. As particularly shown in FIG. 1, the preferred position of the member 10 is spaced from the tympanic membrane or ear drum 20, cochlea 22, semicircular canals 24, stapes 26, incus or anvil 28, and the malleus or hammer 30. In this manner, the prosthesis can perform its regulating function without interfering with the operation of those portions of the ear noted above. Once the prosthesis member is positioned at this eustachian tube/middle ear cavity interface, the member will ideally retain its position without further human intervention. Other arrangements for securing the prosthesis member 10 in the eustachian tube can be used without departing from the scope and intent of the subject invention even though the tapered conformation is considered the most preferred.

With continued reference to FIGS. 1 and 2, and additional reference to FIG. 3, it is apparent that the prosthesis member 10 is a hollow member defining a selectively pressurized interior chamber 34. At least the first end 12, preferably the entire elongated member 10, has a flexible sidewall 36 such that selective pressurization of chamber 34 expands the sidewall 36 into abutting, sealing engagement with the interior wall 40 of the eustachian tube. Conversely, selective deflation of the inflatable member 10 contracts the sidewall from its sealing engagement with the eustachian tube wall 40.

The prosthesis device is formed from a material that is physiologically inert or compatible with the human body. Communicating line or passage 46 extends from the inflatable member 10 to a pump means 48. The pump means 48 is preferably a manually actuated type pump such as sold as a part of the urinary prosthesis by American Medical Systems under the trademark "AMS Sphincter 800". Applicant believes that the pump means is disclosed in U.S. Pat. No. 4,222,377 issued Sept. 16, 1980 to Burton which is hereby incorporated by reference. The second communication line or passage 50 is interposed between the pump means and a reservoir means 52. The reservoir means is also inflatable being preferably formed of a flexible material. It is also contemplated that the pump means can comprise an automated, self-regulating structure in which a pressure sensing means operatively engages the pump. Suitable microchip control can regulate automated inflation and deflation of the inflatable member in response to signals received from the pressure sensing means disposed in the middle ear or eustachian tube.

The pump means, reservoir means, and communicating lines define a closed system means for selectively inflating and deflating the inflatable member witha physiologically inert work fluid. One-way or check valves (not shown) are incorporated in the pump means and permit selective communication between the inflatable member and the reservoir means. Still further, a flow restrictor (not shown) is disposed in the pump means to restrict return flow from the reservoir means to the inflatable member as will be described further hereinbelow.

Contrary to prior art methods of treating this condition from the throat end, the prosthesis A of the subject application is inserted from the outer ear end. More specifically, a region 54 is hollowed out of the mastoid 56 through conventional surgical procedure to provide access to the middle ear cavity 18. The inflatable member can thereby be positioned through the mastoid cavity with the first end 12 in the eustachian tube and the enlarged second end 14 extending into the middle ear. The communicating passage 46 is placed in subcutaneous tissue behind the ear and on the skull. Placement of the pump on the skull provides a support or backing surface to facilitate depression of actuating portion 60 of the pump.

A preferred embodiment of the subject invention provides a reservoir 52 separate from but interconnected to the pump. The reservoir is dimensioned for receipt in the mastoid cavity where it does not interfere with the remainder of the prosthesis device and is effectively "hidden" from view upon completion of the surgery.

According to another preferred embodiment, an expansible chamber (not shown) of the pump has sufficient volume so as to define the reservoir means 52. For example, it is contemplated that approximately 0.5 to 1 cc of fluid will define the difference in volume of the inflatable member 10 in its inflated and deflated states. This minute volume of fluid can be incorporated into the design specifications of the pump. Thus, the mastoid cavity need not accommodate a separate reservoir. This change in the prosthesis device is represented by showing the reservoir means and passage 50 in phantom. One of ordinary skill in the art will understand that the function of the prosthesis device is identical no matter which reservoir embodiment is used.

To operate the prosthesis device A, the pump means is activated by pressing down on the actuation portion 60 of the pump through the skin and against the skull. Pressurized fluid is pumped from the inflatable member through a one-way valve to the reservoir means. The inflatable member thereby deflates and permits communication between the middle ear and nasopharynx 62. The pressure imbalance in the closed loop system of the prosthesis want to equilibrate and pressurized fluid passes through a flow restrictor from the reservoir means to the inflatable member. The flow restrictor regulates the time period over which this pressure balancing may take place, typically a few minutes. Once pressure equilibrium is established, the inflatable member is inflated again the sealingly engages the eustachian tube interior wall blocking communication between the middle ear cavity and the nasopharynx.

Selective inflation and deflation of the inflatable member allows a patient to simulate on demand the functions of a normal, healthy eustachian tube. There is no longer a constant and free communication between the nasopharynx and middle ear cavity when the prosthesis member is inflated and yet selective deflation of the inflatable member permits communication between the middle ear and the nasopharynx. The pump means can be actuated volitionally or on demand and it is anticipated that the inflatable member will routinely block communication through the eustachian tube for extended periods of time and remain deflated for only a few minutes a day.

The operation of the prosthesis device A typically will not change when treating a dysfunctional/chronically closed eustachian tube or an abnormally patulous eustachian tube. With either condition, the prosthesis device simulates the operation and function of a normal healthy eustachian tube. It is, though, necessary to suitably modify the chronically closed eustachian tube before implantation of the prosthesis device. The above-described inflatable prosthesis device can then be used as described or in conjunction with other, known, non-regulatory conduits, tubes or stents as described in the U.S. Pat. No. 4,015,607. For example, the inflatable prosthesis member can be positioned in a known stent which is itself closely received in the eustachian tube. Selective inflation and deflation of the inflatable member thereby controls communication between the middle ear and nasopharynx through the stent. Alternately, the stent 70 can be modified as in FIG. 5 to have a generally truncated frustoconical or trumpet-shaped conformation to matingly receive the inflatable member. In all other aspects, the inflatable prosthesis operates as described above. The subject prosthesis device provides volitional and selective control or regulation of the eustachian tube function unlike known prostheses.

The invention has been described with reference to the preferred embodiments and methods. Obviously modifications and alterations will occur to others upon a reading and understanding of this specification. It is intended to include all such modifications and alterations insofar as they come within the scope of the appended claims or the equivalents thereof.

I claim:

1. An implantable eustachian prosthetic system, comprising:
   a generally elongated inflatable member, said inflatable member having a first end defining an inflatable dimension approximating the diameter of the eustachian tube opening for at least partial receipt therein and an opposite second end, designed to retain the inflatable member at the interface between the eustachian tube and the middle ear; and,
   a separate pump means configured to be implanted and operatively coupled to said inflatable member, said pump means adapted for selectively inflating and deflating said inflatable member after said inflatable member is implanted so as to selectively permit and prevent communication from the middle ear through the eustachian tube.

2. The prosthesis as defined in claim 1 wherein said inflatable member has a generally tapered conformation over its longitudinal dimension between said second end and said first end.

3. The prosthesis as defined in claim 1 wherein said pump means includes a reservoir means and pump member operatively associated with said inflatable member.

4. The prosthesis as defined in claim 1 wherein said pump means includes a reservoir means and pump member in closed loop relation with said inflatable member, actuation of said pump member increasing the volume of a work fluid in said reservoir means as said inflatable member deflates.

5. A eustachian tube prosthesis assembly sized for at least partial receipt in a patient's eustachian tube and regulating communication between the middle ear and nasopharynx, said prosthesis assembly comprising:
   an inflatable member dimensioned for at least partial receipt in an associated eustachian tube;
   a stent adapted to be operatively interposed between said inflatable member and the eustachian tube; and,
   means for selectively inflating and deflating said inflatable member to regulate communication through the eustachian tube.

6. An implantable eustachian tube prosthetic system comprising:
   a generally elongated inflatable member, said inflatable member having a first end defining an inflated dimension approximating the diameter of the eustachian tube opening for at least partial receipt therein and an opposite second end, designed to retain the inflatable member at the interface between the eustachian tube and the middle ear;
   a stent adapted to be operatively interposed between said inflatable member and the eustachian tube; and,
   a separate pump means configured to be implanted and operatively coupled to said inflatable member, said pump means adapted for selectively inflating and deflating said inflatable member after said inflatable member is implanted so as to selectively permit and prevent communication from the middle ear through the eustachian tube.

7. The prosthesis assembly as defined in claim 6 wherein said stent has a generally trumpet-shaped conformation.

8. The prosthesis assembly as defined in claim 6 wherein said stent has an outer periphery dimensioned to be closely received in the eustachian tube.

9. The prosthesis assembly as defined in claim 6 wherein said inflatable member has a generally tapered conformation over its longitudinal dimension between opposed first and second ends.

10. The prosthesis assembly as defined in claim 6 wherein said pump means includes a reservoir means and pump member operatively associated with said inflatable member.

11. The prosthesis assembly as defined in claim 10 wherein said reservoir means and pump member are disposed in closed loop relation with said inflatable member.

* * * * *